United States Patent [19]

Wynne et al.

[11] Patent Number: 5,507,760
[45] Date of Patent: Apr. 16, 1996

[54] CUTTER DEVICE

[75] Inventors: Robert L. Wynne, Pacifica; David W. Snow, Menlo Park; Larry B. Rogers, Half Moon Bay; Ferolyn Powell, San Carlos; Jeffrey W. Krier, El Granada; Ron Hundertmark, San Mateo; Earl R. Hill, III, Berkeley; Randolph E. Campbell, Encinitas, all of Calif.

[73] Assignee: Devices for Vascular Intervention, Inc., Redwood City, Calif.

[21] Appl. No.: 149,587

[22] Filed: Nov. 9, 1993

[51] Int. Cl.$^6$ .................................................. A61B 17/32
[52] U.S. Cl. ................................................ 606/159; 606/170
[58] Field of Search .................................. 606/159, 167, 606/170, 171, 180; 604/22

[56] References Cited

U.S. PATENT DOCUMENTS

| | | | |
|---|---|---|---|
| 4,669,469 | 6/1987 | Gifford, III et al. | 606/159 |
| 5,085,662 | 2/1992 | Willard | 606/159 |
| 5,100,424 | 3/1992 | Jang et al. | 606/159 |
| 5,160,318 | 11/1992 | Shuler | 604/22 |
| 5,242,460 | 9/1993 | Klein et al. | 604/22 |

Primary Examiner—Stephen C. Pellegrino
Assistant Examiner—William W. Lewis
Attorney, Agent, or Firm—Douglas A. Chaikin

[57] ABSTRACT

Disclosed herein is a cutter capable of removing soft and hard tissue when used with an atherectomy catheter of the type having a cutter housing attached to the distal end of a catheter having a torque cable. A circular cutting blade is disposed within the housing and is secured to the distal end of a rotatable torque cable. An elongated aperture formed along one side of the hosing allows the intrusion of stenotic material which may then be severed by rotating and axially translating the cutting blade. The cutting blade may be made from a cemented tungsten carbide compound of 90 percent tungsten carbide (WC) and 10 percent cobalt (Co) which is heated, injection molded and sintered to produce a hard, durable cutting edge. The cutting edge is coated with titanium carbonitride using a physical vapor deposition process to further increase durability. Cutting edge hardness is further increased by application of an ion implantation of nitrogen using an ion-beam assisted deposition process. A variety of alternative cutter materials, coatings and geometries are defined which improve cutter performance in removing soft and hard lesions.

20 Claims, 4 Drawing Sheets

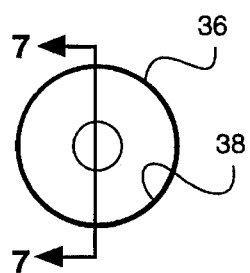 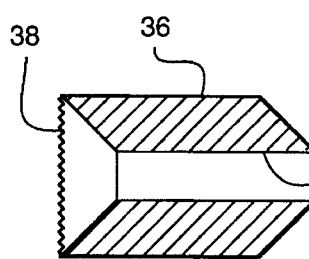 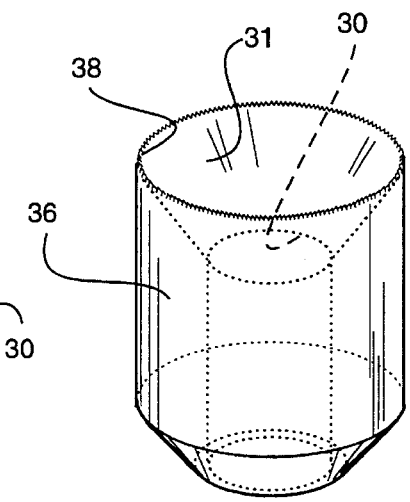
FIG. 6  FIG. 7  FIG. 8
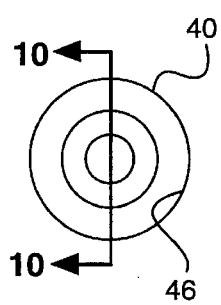 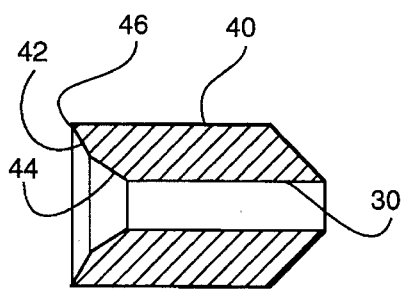 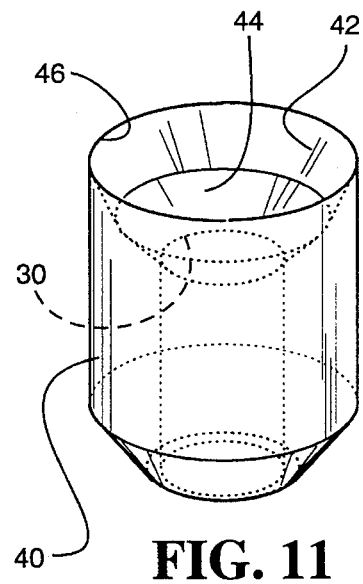
FIG. 9  FIG. 10  FIG. 11

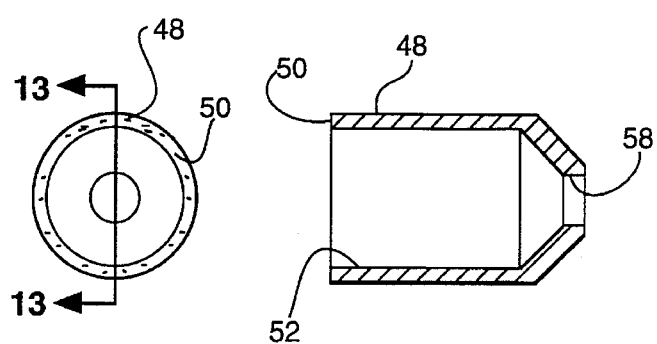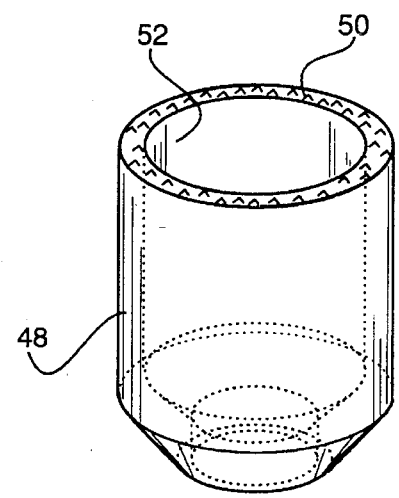
FIG. 12  FIG. 13  FIG. 14
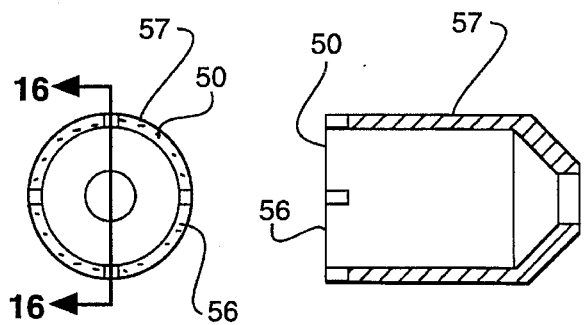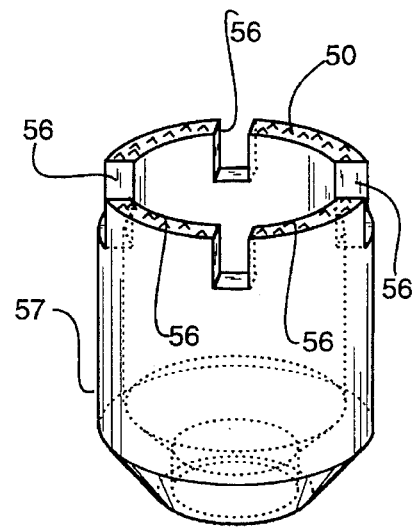
FIG. 15  FIG. 16  FIG. 17

5,507,760

CUTTER DEVICE

RELATED APPLICATION

This application incorporates by reference copending U.S. application, Ser. No. 08/091,160, filed Jul. 13, 1993, entitled "Imaging Atherectomy Apparatus," which is a continuation-in-part of U.S. application, Ser. No. 08/051,521, filed Apr. 21, 1993, now abandoned.

BACKGROUND OF THE INVENTION

1. Field of the Invention

This invention relates to biological tissue cutters for use with atherectomy devices inserted into a biological conduit for removal of diseased tissue, and specifically relates to cutters adapted for removal of both calcified soft tissue.

2. Previous Art

Atherosclerosis is a condition characterized by fatty deposits (atheromas) in the intimal lining of a patient's blood vessels. Atherosclerosis can present in a variety of ways including angina, hypertension, myocardial infarction, strokes, and the like. Regions of the blood vessel which are blocked by atheroma, plaque, or other material are generally referred to as stenoses, and the blocking material as stenotic material. The atheromas deposited on the blood vessel walls are often relatively soft and tractable. However, in many cases the atheromic material is a calcified and hardened plaque. Removal of the calcified tissue by current atherectomy is extremely difficult.

Atherectomy is a procedure which has been developed for removing stenotic material from the vascular system, usually before substantial calcification has occurred. Atherectomy procedures utilize a variety of special catheters having tissue cutting members (cutters) located at a distal end. In use, the catheter is inserted into a biological conduit of the vascular system so that the cutter is adjacent to the stenotic region. The cutter is then manipulated to excise a portion of the stenotic material. The severed material is captured to prevent the release of emboli into the blood stream.

The tissue cutting member on an atherectomy catheter can take a variety of forms, including fixed blades (requiring movement of the entire catheter to effect cutting) and movable blades which are manipulated within a stationary housing at the distal end of the catheter.

Of particular interest to the present invention are atherectory catheters of the type described in copending U.S. continuation-in-part application, Ser. No. 08/091,160, filed Jul. 13, 1993 by Milo et al., entitled "Imaging Atherectomy Apparatus," hereby incorporated by reference. These atherectomy catheters include a cutter housing attached to the distal end of a torquable catheter body. A circular cutting blade is disposed within the housing and is secured to the distal end of a rotatable drive shaft (torque cable). "Torque cable" is a general term in the art which refers to any means used to rotate and advance the cutting blade of the catheter. An elongated aperture (window) formed along one side of the housing allows the intrusion of stenotic material which may then be severed by rotating and axially translating the cutting blade.

The use of such atherectomy catheters has been limited primarily to removal of non-calcified stenotic material. Not infrequently however, an interventionist (physician) is confronted with a need to remove tissue including calcified deposits. The hardness of these deposits can be comparable to that of the material used to make the current cutting blade. Therefore, attempts to use atherectomy catheters to remove calcified tissue result in the cutting edge becoming rounded and dulled and is thereby rendered ineffective to remove non-calcified (soft) tissue.

What is needed is a cutting blade which is effective for cutting soft tissue.

What is also needed is a cutting blade durable enough to retain its soft tissue cutting ability when used to remove calcified tissue.

What is also needed is a cutting blade made of a material hard enough not to break.

Finally, what is needed is a cutting blade that is biocompatible.

SUMMARY OF THE INVENTION

It is an object of this invention to provide a cutter which is hard enough to cut and remove calcified tissue, and durable enough to retain a cutting edge which can effectively excise soft tissue.

It is an additional object of this invention to make a cutting blade hard enough not to break while cutting calcified tissue.

It is an additional object of this invention to provide a cutting blade which is biocompatible.

In accordance with the above objects and those that will be mentioned and will become apparent below, a cutter for use in excising plaque within a biological conduit and being adaptable for connection with a catheter having a torque cable is provided, comprising:

a body having a cutting edge and being adaptable for attachment to the torque cable and an exterior portion which contacts the biological conduit;

the body being made of a material selected from the group consisting of tungsten carbide, cermet, carbide-based cermets, polycrystalline cubic boron nitride, aluminum oxide, and silicon nitride; and at least the exterior portion of the cutter being biocompatible, whereby the cutting edge, being made of a hard, durable material, is capable of cutting calcified and soft tissue.

In a preferred embodiment, the cutter body is made from a cemented tungsten carbide mixture of 90 percent tungsten carbide and 10 percent cobalt (90WC-10Co). The cutter body is cylindrical, has proximal and distal ends and an axis extending between the ends. The distal end has a cup shaped recess, the recess being generally symmetrical about the axis. The cylinder has an outer surface which includes an outer wall portion. The proximal end and outer wall portion of the cylinder is adapted to fit compatibly within a cylindrical housing of the distal end of the catheter. The body and the cutting edge of the 90WC-10Co cutter are coated with a biocompatible material selected from the group consisting of titanium carbonitride and titanium nitride. This coating increases durability resistance to fragmentation.

In another embodiment, the cutting edge of a coated 90WG-10Co cutter is treated by ion implantation of nitrogen. This implantation further increases the performance of the cutting edge.

In another embodiment, the cutter is made of a stainless steel and is coated with a biocompatible substance which increases the hardness of the cutting edge.

In another embodiment, the cutter is made of a stainless steel and the surface is treated by a process such as ion implantation to increase the hardness and the overall cutting performance of the cutting edge.

A number of alternative cutting edge geometries are defined, and a method for hardening the stainless steel cutting edge by heat treating is presented.

It is an advantage of the present invention to provide a cutter capable of effectively excising both calcified (hard) and non-calcified (soft) tissue.

It is a further advantage of the present invention to provide a cutter having a cutting edge hard enough not to break when used to remove hard lesions.

It is also an advantage of this invention to provide a cutter which is biocompatible.

BRIEF DESCRIPTION OF THE DRAWING

For a further understanding of the objects and advantages of the present invention, reference should be had to the following detailed description, taken in conjunction with the accompanying drawings, in which like parts are given like reference numerals and wherein:

FIG. 6 is an end view of an alternative embodiment of the cutter of FIGS. 3–5 and having a serrated cutting edge.

FIG. 7 is a side sectional view of the cutter of FIG. 6 taken along line 7—7 and looking in the direction of the arrows.

FIG. 8 is a perspective view of the cutter of FIGS. 6, 7.

FIG. 9 is an end view of another alternative embodiment of the cutter of FIG. 2 and having a cup shaped compound angle single arcuate cutting edge.

FIG. 10 is a side sectional view of the cutter of FIG. 9 taken along line 10—10 and looking in the direction of the arrows.

FIG. 11 is a perspective view of the cutter of FIGS. 9, 10.

FIG. 12 is an end view of another alternative embodiment of the cutter of FIG. 2 and having a flat-lapped, abrasive cutting surface.

FIG. 13 is a side sectional view of the cutter of FIG. 12 taken along line 13—13 and looking in the direction of the arrows.

FIG. 14 is a perspective view of the cutter of FIGS. 12, 13.

FIG. 15 is an end view of another alternative embodiment of the cutter of FIGS. 12–14 and including cutting teeth along the abrasive, flat-lapped cutting surface.

FIG. 16 is a side sectional view of the cutter of FIG. 15 taken along line 16—16 and looking in the direction of the arrows.

FIG. 17 is a perspective view of the cutter of FIGS. 15, 16.

DETAILED DESCRIPTION OF THE INVENTION

Introduction

Figure 1:
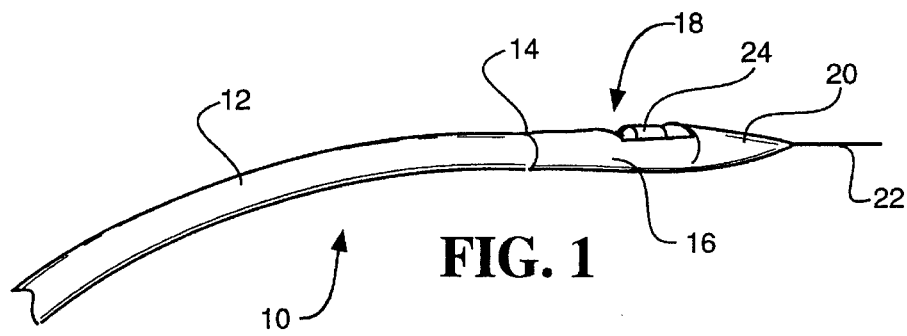
FIG. 1 is a partial perspective view of an atherectomy catheter which uses a cutter in accordance with the present invention.

With respect to FIG. 1, there is shown a partial perspective view of an atherectomy catheter 10 illustrating elongated catheter member 12 having a distal end 14, a second, a cylindrical housing 16 including an opening 18 along one side, a third, a nose cone 20, fourth, a guide wire 22 and, finally, a biological tissue cutter 24.

The distal end 14 of the elongated catheter member 12 is connected to the cylindrical housing 16. The nose cone 20 provides an atraumatic termination. A flexible torque cable 26 (FIG. 2) extends within the catheter member 12 and into the housing 16. The tissue cutting member 24 is attached to the torque cable 26 and is able to rotate and slide freely within the cylindrical housing 16. The guide wire 22 extends through the torque cable 26, through the tissue cutting member 24 and extends distally beyond the end of the nose cone 20.

In use, the atherectomy catheter 10 is inserted into a biological vessel and positioned such that the opening 18 is adjacent to diseased tissue. The torque cable 26 is manipulated to slide the tissue cutting member 24 into the proximal end of the housing 16. The torque cable 26 is then rotated and advanced in the distal direction causing the attached tissue cutting member 24 to rotate and advance, thereby cutting tissue which extends from the conduit wall through the opening 18 and into the cylindrical housing 16. The rotational motion causes the circular cutting edge 28 to slice through the diseased tissue as the cutter 24 is advanced within the housing 16.

Figure 2:
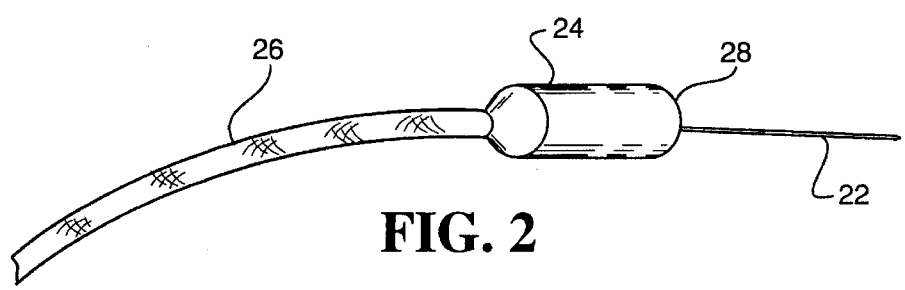
FIG. 2 is a partial perspective view of a torque cable and attached cutter of the atherectomy catheter of FIG. 1.

FIG. 2 is a partial perspective view illustrating a portion of the torque cable 26, the tissue cutting member 24 and the guide wire 22 of FIG. 1. The distal end of the tissue cutting member 24 includes a sharpened, circular cutting edge 28. The cutting edge 28 slices through diseased tissue which extends into the cylindrical housing 16. The torque cable 26 is rotated and is advanced in the distal direction causing the attached tissue cutting member 24 to rotate and advance. The rotational motion causes the circular cutting edge 28 to slice through the diseased tissue as the cutter 24 is advanced within the housing 16.

Figure 3:
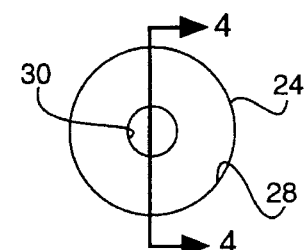
FIG. 3 is an end view of the cutter of FIG. 2 and having a cup shaped single arcuate cutting edge.

FIG. 3 is an end view of a tissue cutting member 24 such as illustrated in FIGS. 1, 2. Cutter 24 includes a cup shaped single arcuate cutting edge 28 and an axial bore 30.

Figure 4:
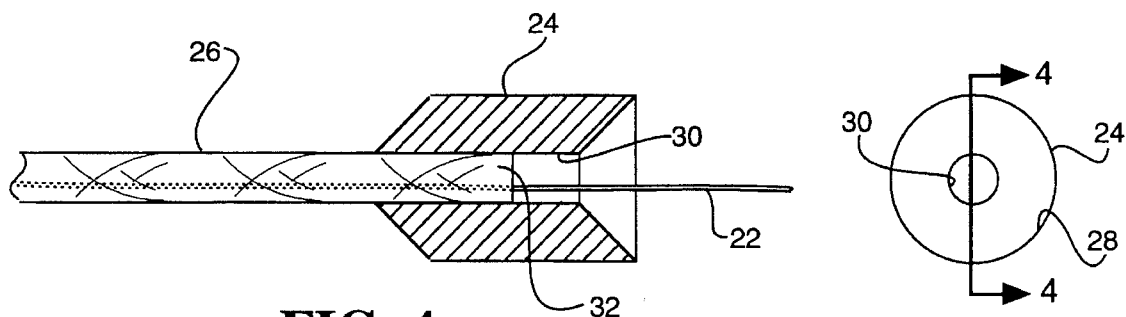
FIG. 4 is a side sectional view taken along line 4—4 of FIG. 3 and looking in the direction of the arrows.

A side sectional view through the line 4—4 of FIG. 3, looking in the direction of the arrows, is illustrated in FIG. 4. The tissue cutting member 24 includes the axial bore 30 whose diameter is adapted to accommodate the distal end 32 of the torque cable 26. The guide wire 22 is shown extending from the distal end 32 of the torque cable 26.

The cutter 24 is secured to the torque cable 26 by one of several methods including adhesive, press fit, or other methods of mechanical retention such as soldering, welding or brazing. In one embodiment, the torque cable 26 is made of a metal and is enclosed within a plastic covering. The plastic covering is removed near the distal end 32 of the torque cable 26 thereby exposing the metal. The distal end 32 is then soldered into the axial bore of the cutter 24.

Figure 5:
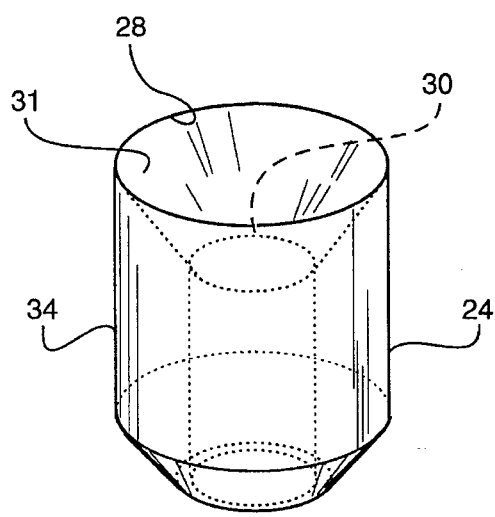
FIG. 5 is a perspective view of the cutter of FIGS. 3, 4.

FIG. 5 is a perspective view of the cutter 24 of FIGS. 3 and 4 illustrating the cup shaped arcuate single cutting edge 28, the axial bore 30, a cup shaped distal recess 31 and an outside wall (outside diameter) 34. The intersection of the cup shaped recess 31 with the outside wall 34 defines the single arcuate cutting edge 28.

FIGS. 1–5 illustrate the tissue cutting member 24 which is the subject matter of the present invention. When cutting calcified diseased tissue with a conventional atherectomy catheter, the circular cutting edge 28 can be easily damaged. The damaged cutting edge 28 is not effective for cutting calcified tissue, nor is it effective for cutting non-calcified (soft) stenotic tissue.

The present invention overcomes the problem of dulling of to the cutting edge 28 in a variety of ways. First to be considered is the use of tough, hard materials for making the tissue cutting member 24. The use of such materials provides a cutting edge 28 which can withstand much of the damage normally inflicted by calcified tissue while retaining the ability to effectively remove soft lesions. Biocompatibility is assured by the use of coatings which also improve performance. Biocompatibility is defined by persons skilled in the art as conforming to the Tripartide Guidelines for biocompatibility.

Second to be considered is a tissue cutting member 24 made of a stainless steel and coated with a material to increase the surface hardness and lubricity. A secondary coating can be applied to selected areas of the cutter 24 to provide an abrasive or grinding capability. Any coating of tissue cutting member 24 is biocompatible.

A third family of embodiments of the present invention relates to "engineered" surface treatments, such as ion implantation of selected materials. These are used to harden or to improve the cutting edge 28 during assembly and maintain it during operation.

Next, a variety of cutting edge 28 geometries are defined which improve the ability of the cutting edge 28 to remove or excise calcified tissue.

Finally, a method for hardening the stainless steel cutting edge by heat treating the tissue cutting member 24 is defined.

Materials

Testing has demonstrated that cutter base materials must meet the following requirements to be effective in removing calcified tissue. The cutter material must be durable enough to retain an effective soft tissue cutting edge while cutting hardened lesions. The cutter material must be hard enough not to break. Finally, the material must be biocompatible, at least where an exterior portion of the cutter is in contact with biological matter, e.g. biological conduit. The former two requirements are unique to the atherectomy catheter application as compared with typical industrial cutting/machining requirements.

Tungsten carbide is a moderately biocompatible material which is capable of cutting hardened lesions without significant degradation of the cutting edge. It retains its cutting edge and resists breakage. Other hard materials are known to posses similar properties.

Therefore, in one embodiment, the cutter body 24 is made of a material selected from the group including but not limited to tungsten carbide, cermets, carbide-based cermets, polycrystalline cubic boron nitride, aluminum oxide and silicon nitride.

"Cermet" is an acronym used to designate a heterogeneous combination of metal(s) or alloy(s) with one or more ceramic phases in which there is relatively little solubility between metallic and ceramic phases at the preparation temperature. Carbide-based cermets constitute the bulk of the cermets. This group includes the cemented carbide cutting tools and wear parts based on tungsten carbide. These materials are described in Vol. 7, Metals Handbook, 9th edition, "Powder Metallurgy," American Soc. for Metals, 1984, which is specifically incorporated herein by reference.

Preferably the cutter body 24 is made of 90 percent tungsten carbide (WC)and 10 percent cobalt (Co). The tungsten carbide is in the form of a powder having particles of a diameter averaging 0.6 micron. The mixture of tungsten carbide powder and cobalt is placed in a mold and then pressed and heated ("sintering") in a well-defined process of producing cemented carbides. In most industrial applications, 6 percent cobalt is used for a similar purpose. The 10 percent cobalt mixture of the present invention makes the resulting material more durable and thus better able to resist breaking and chipping.

The 90WC-10Co cutter body 24 is only moderately biocompatible. When coated with titanium carbonitride or titanium nitride however, the 90WC-10Co body 24 passes the Tripartide Guidelines for biocompatibility inert.

Coatings

The cutter body 24 may be completely or selectively coated with materials which improve the cutting capabilities of the base material. Relative to the harder materials which have been described above, a coated steel cutter has been shown to be easier to manufacture and has produced similar performance results. Stainless steel cutters made of both 440 FSe of 440 C stainless steel in combination with coatings have been shown to cut through calcified material while retaining their edges.

Properties provided by the coatings include increased hardness (abrasive resistance) and improved surface finish (lubricity). Additive material shown to improve performance include diamond-like carbon, alumina, titanium nitride, titanium carbonitride, zirconium nitride, boron nitride, cubic boron nitride and high chromium-composites such as ME-92, as well as other proven surface engineered treatments. ME-92 can be purchased from Electrolizing, Inc., 10 Houghton St., Providence, R.I. 02904.

Selectively coating certain portions of the cutter 24 can be shown to provide different functional zones on the cutter. For example, coating the cup shape recess 31 of the cutter 24 (FIG. 5) with an abrasive material such as polycrystalline diamond and coating the edge with a hard material, such as titanium nitride, will provide a cutter with the ability to cut the calcified material and also grind the calcified material as it bottoms out in the cup shaped recess 31. This combination allows concurrent cutting and removal of the calcified material. Coating the outside diameter 34 of the cutter 24 with a hard, smooth coating can improve the bearing interface with the inside of the housing.

In a preferred embodiment, the cutting edge 28 of the 90WO-10Co cutter 24 is coated with a titanium carbonitride using a process such as the Baizers TiCN coating process (Baizers Tool Coating Inc., North Tonawanda, N.Y.). Alternatively, the cutter 24 is coated with a titanium nitride using a process such as the Baizers TiN process. The coating is a multiple layer thin film coating formed in a low temperature PVD (physical vapor deposition) process. The preferred coating thickness is approximately 2.5 microns. The resulting coating edge has a thickness of approximately 5–10 microns.

Engineered Surfaces

Implantation of certain materials into the cutter base materials increases the hardness of the base material. Materials to be implanted include nitrogen, boron and other elements that enhance the hardness, wear resistance, biocompatibility and general application efficiency. These other elements include chromium, carbon, titanium and nitrogen. The implantations are made using a surface engineered process such as ion-beam assisted deposition (IBAD) or ion implantation.

In one embodiment, an increase in cutting edge 28 hardness without significant decrease of durability has been noted for a 90WC-10Co base material coated with titanium carbonitride or titanium nitride and treated with an ion implantation of nitrogen.

Cutter Geometries

FIGS. 3–5 define the basic cup shaped single arcuate cutting edge 28 which has been demonstrated to be an effective cutter geometry for the removal of material modeled after heavily calcified stenotic tissue. Additional cutter geometries have been investigated for this purpose and are presented in FIGS. 6 through 26.

A pair of variations of the single arcuate cutting edge cutter are illustrated in FIGS. 6–11. FIG. 6 is an end view of a cutter having a serrated cutting edge 38. The teeth of this cutting edge are designed to be effective at removing calcified tissue. FIG. 7 is a side sectional view taken through line 7—7 of FIG. 6 and looking in the direction of the arrows. Cutter 36 includes the axial bore 30 used for connection of the cutter to the distal end of a torque cable 32. FIG. 8 is a perspective view of the cutter 36 illustrated in FIGS. 6, 7. The serrated cutter 36 includes a cup shaped distal recess 31.

FIG. 9 is an end view of a cup shaped compound angle single arcuate edged cutter 40. A side sectional view of the cutter 40 taken through the line 10—10 of FIG. 9 and looking in the direction of the arrows is illustrated in FIG. 10. A cup shaped distal recess includes compound right frustrum sections 42 and 44. The compound arrangement allows significant cup depth while the body material near the cutting edge 46 retains a greater thickness than is possible with a simpler geometry. The increased thickness improves the ability to withstand chipping and fragmentation of the cutting edge 46 when used to remove heavily calcified material. FIG. 11 is a perspective view of the compound angle cutter 40 of FIGS. 9 and 10. The cutter 40 includes the axial bore 30.

FIGS. 12–17 illustrate cutters having a hollow cylindrical body and a flat-lapped cutting surface. This flat-lapped cutting surface may be abrasive, but it does not have to be. If the cutter having this geometry removes a calcified deposit it with an abrasive cutting surface, then removal of a calcified deposit by the abrasive cutting surface may be by grinding, but it does not have to be. FIG. 12 is an end view of a cutter 48 having an abrasive cutting surface 50 which is coated with an abrasive material such as diamond grit. The abrasive material may be applied to the cutting surface 50 using a physical vapor deposition process or the like or can be ion implanted as described above. FIG. 13 is a side sectional view along line 13—13 of FIG. 12 looking in the direction of the arrows. The cutter 48 includes a hollow interior 52 having a short axial bore 54 at the proximal end for attachment to a torque cable. The hollow interior 52 permits the collection of much removed tissue not possible with the more shallow cup shaped recess of other geometries. FIG. 14 is a perspective view of the cutter 48 showing an abrasive cutting surface 50 and a portion of the hollow interior 52.

In FIGS. 15–17, the flat-lapped abrasive cutting surface 50 includes a plurality of cutting teeth 56. FIG. 15 is an end view, FIG. 16 is a side sectional view along line 16—16 of FIG. 15, and FIG. 17 is a perspective view of the cutter 57.

Figure 18:
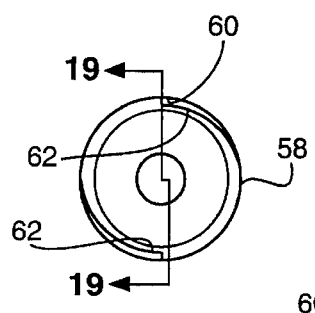
FIG. 18 is an end view of another alternative embodiment of the cutter of FIG. 2 and including a flat-lapped, single cutting edge having a pair of spiral members.
Figure 19:
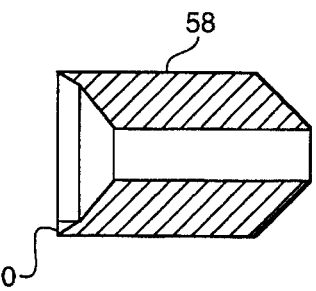
FIG. 19 is a side sectional view of the cutter of FIG. 18 taken along line 19—19 and looking in the direction of the arrows.
Figure 20:
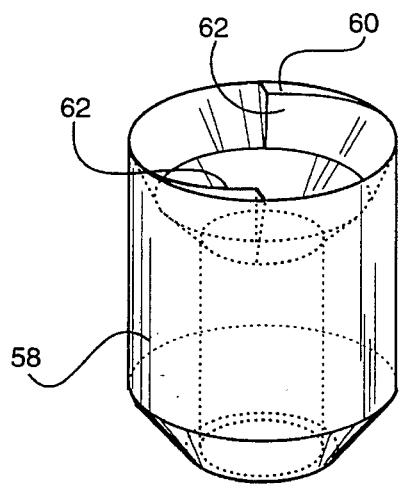
FIG. 20 is a perspective view of the cutter of FIGS. 18, 19.

FIGS. 18–20 illustrate a cutter 58 having a flat-lapped single cutting edge 60. As illustrated in a side sectional view, FIG. 19, and in a perspective view, FIG. 20, the single cutting edge 60 includes a pair of spiral members 62 whose thickness decreases to a single arcuate cutting edge within 90 degrees of rotation. The distal surface of the spiral members 62 is flat lapped for cutting calcified material.

Figure 21:
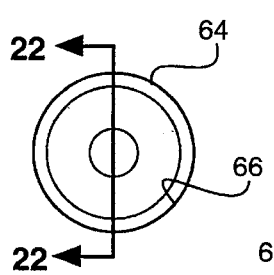
FIG. 21 is an end view of another alternative embodiment of the cutter of FIG. 2 and having a curvilinear varying height cutting edge.
Figure 22:
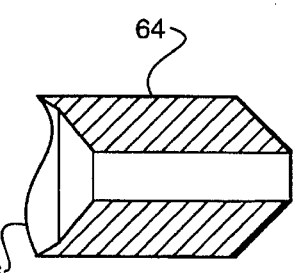
FIG. 22 is a side sectional view of the cutter of FIG. 21 taken along line 22—22 and looking in the direction of the arrows.
Figure 23:
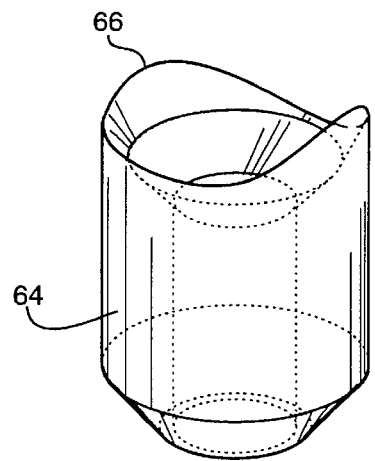
FIG. 23 is a perspective view of the cutter of FIGS. 21, 22.
Figure 24:
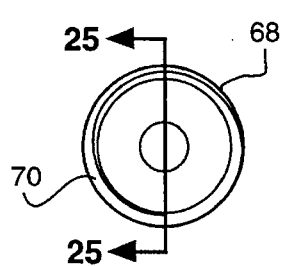
FIG. 24 is an end view of another alternative embodiment of the cutter of FIG. 2 and having a spiral varying height cutting edge.
Figure 25:
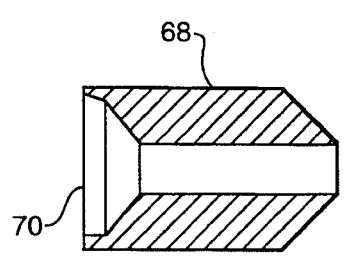
FIG. 25 is a side sectional view of the cutter of FIG. 24 taken along line 25—25 and looking in the direction of the arrows.
Figure 26:
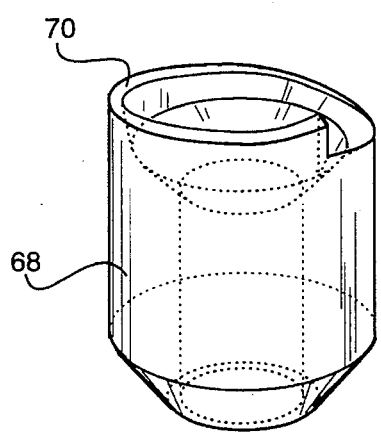
FIG. 26 is a perspective view of the cutter of FIGS. 24, 25.

FIGS. 21–26 illustrate two cutters having non-uniform cutting heights. FIGS. 21–23 show a cutter 64 having a curvilinear cutting edge 66 whose height varies to reduce damage to the edge resulting from constant contact with calcified tissue. FIGS. 24–26 illustrate a cutter 68 having a spiral varying height cutting edge 70. The cutting edge 70 is flat-lapped and decreases in width to a single cutting edge.

The cutters 58, 64, 68 illustrated in FIGS. 18–26 can be manufactured by a process of metal injection molding. The cutters 58, 64, 68 can also be manufactured using processes such as electrical discharge machining (EDM), chemical etching, photo-laser etching, or assembled as composite structures using separate, joined pieces.

Hardening by Heat Treatment

The cutting edge of each of the cutter geometries is typically sharpened. The edge retention of a sharpened cutting edge can also be improved by various heat treating techniques. In one embodiment, a stainless steel cutter body is heat treated both before and after sharpening. Such treatment has been shown to improve performance in cutting tissue plaque. The hardened cutter 24 has been shown to maintain its narrow cutting edge better than a similar cutter which has not been hardened.

Suitable methods for heat treating stainless steel are provided in the ASM Handbook, Vol. 4, Heat Treating, "Heat Treating of Stainless Steels and Heat-Resistance Alloys," pages 77–782, ASM International, 1991, which is specifically incorporated herein by reference.

While the foregoing detailed description has described several embodiments of the calcification cutter in accordance with this invention, it is to be understood that the above description is illustrative only and not limiting of the disclosed invention. Particularly, the specific geometry of the cutter may vary from those illustrated so long as the cutter retains a generally cylindrical configuration having a cutting edge at one end of the cylinder. Also, the manner in which the torque cable is attached to the cutter may differ from those described. It will be appreciated that variations in the selection of the cutter body material, thickness and type of coating, the portion of the body coated, and the use of a surface implantation or heat treatment to increase hardness can be selected from the range of parameters described and the resulting cutter remains within the scope and spirit of this invention. Thus the invention is to be limited only by the claims as set forth below.

What is claimed is:

1. A cutter for use with a catheter having a torque cable, the cutter comprising:
   a body defining a cutting edge, the body adapted for attachment to the torque cable;
   the body being made of a steel selected from the group consisting of 440 FSe steel and 440 C steel; and
   the body defining a surface, the surface, including the cutting edge being ion implanted with a material selected from the group consisting of nitrogen and boron,
   whereby the cutting edge is capable of cutting calcified tissue.

2. The cutter of claims 1, wherein the cutting edge is sharpened.

3. The cutter of claims 1, wherein the cutting edge is hardened by heat treating.

4. The cutter of claims 1, wherein the cutting edge is hardened by heat treating and is sharpened.

5. The cutter of claim 1, wherein the body is cylindrical, has a proximal end and a distal end, has an axis extending between the ends, and wherein the distal end includes a cup shaped recess, the recess being generally symmetrical about the axis, and wherein the body defines a surface having an outer wall.

6. The cutter of claim 1, wherein the body is cylindrical, has a proximal end and a distal end, has an axis extending between the ends, and wherein the distal end includes a cup shaped recess, the recess being generally symmetrical about the axis, and wherein the body defines a surface having an outer wall.

7. The cutter of claim 1, wherein the body is cylindrical, has a proximal end and a distal end, has an axis extending between the ends, and wherein the distal end includes a cup shaped recess, the recess being generally symmetrical about the axis, and wherein the surface includes an outer wall.

8. The cutter of claims 5, 6 or 7, wherein the cylindrical body includes an axial bore extending therethrough.

9. The cutter of claims 5, 6 or 7, wherein the cup shaped recess intersects the outer wall and wherein the cutting edge is further defined by the intersection of the recess with the outer wall.

10. The cutter of claim 9, wherein the cutting edge is a single arcuate edge.

11. The cutter of claim 6, wherein the cup shaped recess has an abrasive coating and wherein the cutting edge has a lubricating and hardening coating selected from the group consisting of diamond-like carbon, alumina, titanium nitride, titanium carbonitride, zirconium nitride, boron nitride, cubic boron nitride and high chromium-composites.

12. The cutter of claim 11, wherein the abrasive coating is polycrystalline diamond and wherein the cutting edge is coated with titanium nitride.

13. The cutter of claim 12, further including the outer wall having a coating selected from the group consisting of diamond-like carbon, alumina, titanium nitride, titanium carbonitride, zirconium nitride, boron nitride, cubic boron nitride and high chromium-composites.

14. A carbide cutter used with a catheter device for cutting calcified and soft tissue, the cutter comprising:
    a hollow cylindrical body having a proximal end, a distal end, and a central axis extending through the body from one end to the other, the cylindrical body having a surface including an outer wall;
    the proximal end of the body being adapted for attachment to a cutter torque cable;
    the distal end of the body having a cup shaped recess, the recess being generally symmetrical about the axis, the intersection of the recess with the outer wall defining a tissue cutting edge;
    the cutting edge being sharpened; and
    the body material comprising 90% tungsten carbide (WC) and 10% cobalt (CO) and including a biocompatible coating covering a pre-determined portion of the body including the cutting edge, the coating being selected from the group consisting of titanium carbonitride and titanium nitride.

15. The carbide cutter of claim 14, further including a predetermined portion of the surface, including the cutting edge, being ion implanted with nitrogen.

16. The carbide cutter of claim 14, further including means for increasing the hardness of the cutting edge to improve removal of calcified and non-calcified tissue.

17. The carbide cutter of claim 16, wherein the the cutting edge has a coating with a material selected from the group consisting of titanium carbonitride and titanium nitride.

18. The carbide cutter of claim 17, wherein the coated cutting edge implanted with nitrogen.

19. The carbide cutter of claim 14, further including means for increasing the durability of the cutting edge to minimize the potential for fragmentation of the cutting edge during removal of calcified tissue.

20. The carbide cutter of claim 19, wherein the means for increasing durability includes coating the cutting edge with a material selected from the group consisting of titanium carbonitride and titanium nitride.

* * * * *